United States Patent [19]

Bell et al.

[11] Patent Number: 5,414,146

[45] Date of Patent: May 9, 1995

[54] MULTIZONE CATALYTIC PROCESS

[75] Inventors: Weldon K. Bell, Pennington; Steven H. Brown, Princeton, both of N.J.; Mohsen N. Harandi, Langhorne; Jeffrey C. Trewella, Kennett Square, both of Pa.

[73] Assignee: Mobil Oil Corporation, Fairfax, Va.

[21] Appl. No.: 109,971

[22] Filed: Aug. 23, 1993

[51] Int. Cl.⁶ .............................................. C07C 41/06
[52] U.S. Cl. .............................. 568/697; 203/DIG. 6
[58] Field of Search .................. 568/697; 203/DIG. 6

[56] References Cited

U.S. PATENT DOCUMENTS

| 4,605,787 | 8/1986 | Chu et al. | 568/697 |
| 4,886,918 | 12/1989 | Sorensen et al. | 568/697 |
| 4,962,239 | 10/1990 | Bell et al. | 568/697 |
| 5,015,782 | 5/1991 | Harandi et al. | 568/697 |
| 5,091,590 | 2/1992 | Harandi et al. | 568/697 |
| 5,243,102 | 9/1993 | Marker et al. | 568/697 |

Primary Examiner—Howard T. Mars
Attorney, Agent, or Firm—Alexander J. McKillop; Malcom D. Keen; L. Gene Wise

[57] ABSTRACT

Porous metallosilicate catalyst (e.g. Zeolite Beta) is active at low temperature for converting lower alkanol (e.g. methanol) and $C_4$-$C_7$ tertiary alkenes to high octane ether product. Such catalytic reaction is especially useful in multizone catalytic reactor systems employing catstill rectification.

7 Claims, 2 Drawing Sheets

MULTIZONE CATALYTIC PROCESS

BACKGROUND OF THE INVENTION

This invention relates to ether production employing a catalytic distillation technique. In particular, it relates to synthesis of unsymmetrical ethers, such as methyl t-butyl ether (MTBE) or t-amyl alkyl ether by reaction of a lower alkanol with a tertiary alkene in a multizone fixed bed reactor, such as a catalytic distillation ("catstill") tower.

There is a need for an efficient catalytic process to manufacture ethers from the reaction of light olefins with lower alkanols augmenting the supply of high octane blending stocks for gasoline. Relatively low molecular weight ethers such as methyl-t-butyl ether (MTBE) and t-amyl methyl ether (TAME) are in the gasoline boiling range and are known to have a high blending octane number. The present invention provides an improved process for the catalytic reaction of isoalkenes (branched olefins) with lower alkanols (e.g. $C_1$-$C_4$ primary aliphatic alcohols) to provide ether(s). More particularly, the invention relates to a process for the reaction of one or more tertiary olefins such as isobutene, isopentene(s), isohexene(s), etc., or mixtures thereof, with one or more lower alkanols, e.g., methanol, ethanol, n-propanol, isopropanol, etc., or mixtures thereof, to provide one or more ethers employing the acidic form of a particular synthetic porous acidic catalyst material as catalyst. The product ethers are useful as high octane blending stocks for gasoline.

While the use of catstill units has contributed greatly to industrial application of catalytic etherification process employing volatile alkanol and isoalkene reactants, the operating conditions of catstill units require a substantial vertical temperature gradient in the catalytic reaction zone. This variable temperature has a significant effect on reaction kinetics. Conventional etherification processes use as catalyst a macroreticular cation exchange resin in the hydrogen form, such as "Amberlyst 15". A resin catalyst gives a range of about 65° to 90° C. In existing conventional catstill designs, an upper rectifying section utilizes trays or packing rather than catalyst solids due to decrease in catalyst activity at lower operating temperature, i.e., below about 65° C. (150° F.). Since etherification reactions have an equilibrium which favors ether production at lower temperature, it is desirable to employ catalysts and reaction conditions which permit low temperature operation.

It has been discovered that certain acid metallosilicates have catalytic activity for the desired etherification reaction at temperature not greater than 65° C., thus permitting the advantageous catalytic reactions to take place in an upper rectification zone of a multizone catalytic distillation unit. Early catstill units for MTBE production employed sulfonic acid resin solid catalysts in a fixed packed bed supported in a vertical debutanizer tower.

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material.

U.S. Pat. No. 4,605,787 (Chu and Kuehl) discloses the preparation of alkyl tert-alkyl ethers such as MTBE and TAME by the reaction of a primary alcohol with an olefin having a double bond on a tertiary carbon atom employing as catalyst an acidic zeolite having a constraint index of from about 1 to 12, e.g., zeolite ZSM-5, 11, 12, 23, dealuminized zeolite Y and rare earth-exchanged zeolite Y. European Patent Application 55,045 describes a process for reacting an olefin and an alcohol to provide an ether, e.g., isobutene and methanol to provide MTBE, in the presence of an acidic zeolite such as zeolite Beta, zeolites ZSM-5, -8, -11, -12, -23, -35, -43 and -48, and others, as catalyst. U.S. Pat. No. 4,962,239 describes the etherification of olefins with an alcohol over a catalyst comprising a zeolite designated MCM-22. Similar intermediate pore materials may be employed, such as MCM-36, described in U.S. application Ser. No. 07/811,360, filed Dec. 20, 1991, incorporated herein by reference.

Recent efforts in the field of etherification reactions have focused on the use of acid medium-pore zeolite catalyst for highly selective conversion of isoolefin and alcohol starting materials. In U.S. Pat. No. 5,015,782 (Harandi and Owen) zeolitic metallosilicate catalysts such as ZSM-5, ZSM-11, ZSM-12, ZSM-23, ZSM-35, ZSM-50 and zeolite Beta have been reported as desirable high temperature catalysts for MTBE and TAME production. It has been thought that, due to lower acidity as compared to resin catalysts, the zeolites need to be employed at higher reaction temperature to achieve the desired conversion rates. These solid acid catalyst particles are thermally stable, are less sensitive to methanol-to-isobutene ratio, give no acid effluent, and are easily and quickly regenerated.

SUMMARY OF THE INVENTION

An improved continuous process has been found for reacting volatile lower alkanol(s) and tertiary-alkene(s) in a fixed bed multizone reactor vessel to produce corresponding ether(s). In preferred embodiment, the improvement comprises the steps of:

a) maintaining a first bed of solid acid catalyst particles in a lower portion of the catalytic distillation reactor vessel and a second bed of solid acid porous metallosilicate catalyst particles in an upper portion of the reactor vessel, said metallosilicate having a pore size of 5–8 Å and having active Bronsted acid sites;

b) introducing at least one volatile reactant stream and contacting the alkanol and tertiary-alkene with the first bed of solid acid catalyst particles to form ether product under etherification conditions;

c) maintaining catalytic distillation conditions in the first bed of solid acid catalyst particles to condense ether product for recovery as a liquid product stream while vaporizing and transporting unreacted volatile alkanol and tertiary-alkene into contact with the second bed of catalyst particles in an upper portion of the reactor vessel; and d) further reacting the volatile alkanol and tertiary-alkene in the second bed of catalyst particles at a reaction temperature below 65° C. to produce additional ether product.

In the preferred embodiments, the metallosilicate catalyst comprises Zeolite Beta, the alkanol consists essentially of methanol, and the tertiary-alkene comprises isohexene. The fixed bed of diverse catalyst is employed advantageously in a catalytic distillation reactor unit wherein the reactor vessel has a temperature profile to effect product separation from volatile reactants.

The process may be used in converting $C_4$-$C_7$ mixtures in a multizone fixed bed reactor system wherein a first catalyst bed is maintained above 80° C. with either zeolite or resin catalyst to convert $C_5-$ isoalkenes and operatively connected to a cooler second bed of zeolite catalyst for conversion of $C_6+$ isoalkenes.

DETAILED DESCRIPTION OF THE INVENTION

For purposes of discussion, the present inventive process is described with reference to the preparation of methyl isohexyl ether wherein selectivity and yield are increased. Two reaction zones are maintained in vertical serial arrangement. A first lower reaction zone may contain any conventional acid catalyst. A second upper reaction zone contains solid crystalline acid medium-pore metallosilicate catalyst particles. Mixed feedstock containing methanol and isobutene-containing $C_4$ hydrocarbons is contacted with solid catalyst particles in the first reaction zone under etherification conditions to obtain an intermediate product comprising MTBE and unreacted feedstock. The intermediate product is then withdrawn from the first reaction zone and added to the second zone for contact with acid medium-pore metallosilicate catalyst under etherification conditions. A product containing a major amount of TAME is then withdrawn from the second reaction zone. The product is fractionated to obtain a purified TAME which is recovered.

Figure 1:
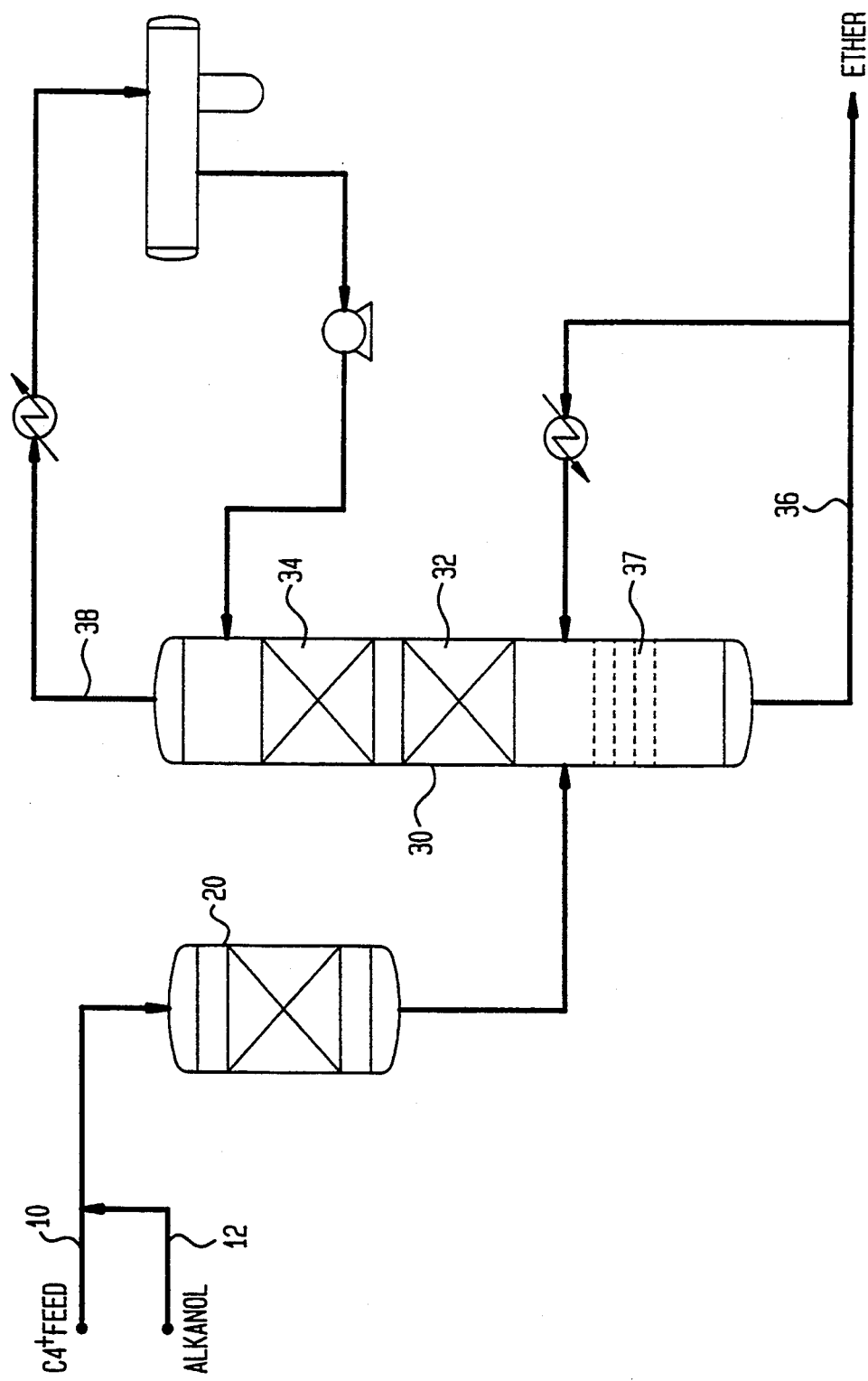
FIG. 1 of the drawing is a schematic process flowsheet depicting the present invention.

Referring to FIG. 1, the inventive process and apparatus are depicted in a flow sheet diagram. The isoalkene feedstream 10 is combined with alkanol feedstream 12 and passed under etherification conditions to an optional conventional first stage fixed bed catalytic reactor 20 for partial conversion of the reactants to provide a first effluent stream comprising ether product, unreacted alkanol and isoalkene. This stream is fed continuously to catalytic distillation unit 30, where a first bed 32 of solid acid catalyst particles is maintained in a lower portion of the catstill reactor vessel 30 and a second bed 34 of solid acid porous metallosilicate catalyst particles in an upper portion of the reactor vessel, said metallosilicate having a pore size of 5-8 Å and having active Bronsted acid sites;

introducing at least one volatile reactant stream and contacting the alkanol and tertiary-alkene with the first bed of solid acid catalyst particles to form ether product under etherification conditions;

Catalytic distillation conditions in the first bed of solid acid catalyst particles are maintained under temperature and pressure conditions to condense ether product for recovery as a liquid product stream 36, while vaporizing and transporting unreacted volatile alkanol and tertiary-alkene upwardly into the secondary metallosilicate catalyst zone 34 for contact with the second bed of solid acid catalyst particles in an upper portion of the reactor vessel, thereby further reacting the volatile alkanol and tertiary-alkene in the second bed of catalyst particles at a reaction temperature below 65° C. to produce additional ether product. The preferred metallosilicate catalyst comprises Zeolite Beta, which is demonstrated to have sufficient activity to convert a major amount of the isoalkene reactant at temperature as low as 50° C. or less.

An overhead vapor stream 38 is recovered from the top of distillation unit 30 and may be condensed as reflux. Unreacted light vapor is recovered from the catstill process, which may contain unreacted alkanol, isoalkene and other light components in the feedstock, such as n-alkenes, alkanes, etc. Various adaptations may be made within the skill of the art, including addition of distillation trays 37 at the bottom of the column 30 or at intermediate or upper locations therein. Bottoms reboiling and overhead reflux are conventional distillation techniques which may be used if desired.

EXPERIMENTS

Figure 2:
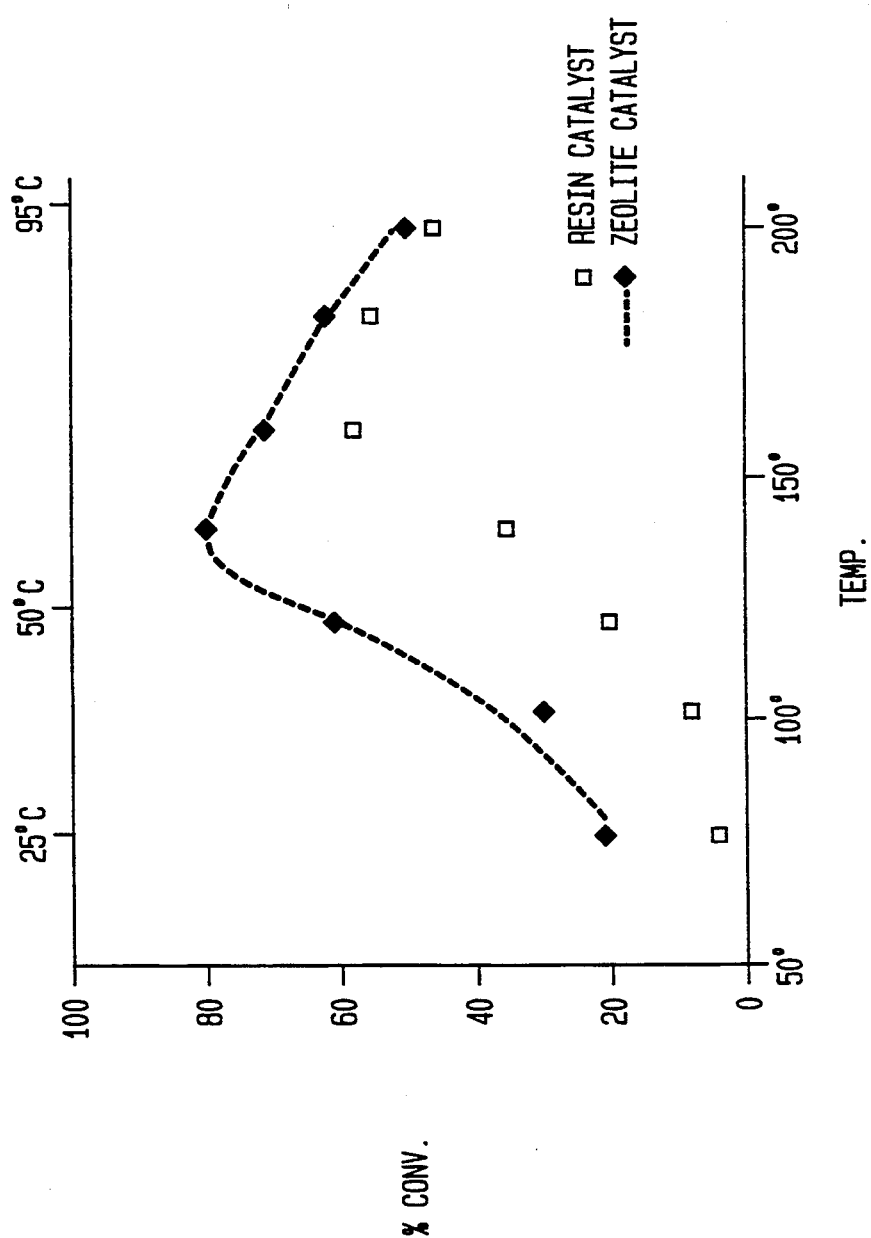
FIG. 2 is a graphic plot of reaction conversion vs. temperature.

A series of comparative experiments were conducted over the temperature range from ambient through the operating range of resin catalyst (about 25° to 95° C.). These runs were conducted in an autoclave at autogenous pressure with methanol and 2-methyl-pentene-1 reactants in a mole ratio of 1.5:1 alcohol:olefin and weight hourly space velocity of 0.6/hr. FIG. 2 is a graphic plot of olefin conversion vs. reaction temperature, comparing Zeolite Beta aluminosilicate catalyst having a pore size of 7.5 Å with commercial polysulfonic acid ("Amberlyst 15") resin catalyst. It is noted that the resin catalyst has consistently lower conversion that the zeolite, peaking at 65° C.+. By comparison, the Zeolite Beta conversion peaks at a lower temperature of 60° C.± and has significantly high conversion even at ambient temperature.

The temperature range below 65° C. is especially important in distillation of the lower alkanols and $C_4$-$C_7$ alkenes. Thus, the present invention enables the skilled chemical engineer to employ active catalyst as a contact solid in the upper portions of a distillation column, where rectification of the more volatile components takes place. This permits a more efficient use of distillation tower capacity for catstill conversion, as contrasted with mere physical separation.

The operating conditions of the multizone catstill etherification unit are important and can include a temperature of from about 25° to about 100° C., preferably from about 40° to 95° C. Most preferably the temperature gradient along the vertical axis of the distillation unit is about 30° C., ranging from a high temperature at the bottom of the lower catstill zone (e.g. resin catalyst) of 65°-90° C. to about 40°-60° C. at the top of the upper catstill zone (e.g. zeolite catalyst), with corresponding decrease in autogenous pressure. The less volatile isoalkenes, such as t-hexene, and heavier alkanols would require a higher overall temperature than the lighter methanol and isobutene reactants. A total system pressure of about 1 to 15 atmospheres is desirable; and alcohol to olefin mole ratio of from about 0.1 to about 5 may be employed, preferably from about 0.2 to about 2 and most preferably from about 0.5 to about 1.2. The space velocity depends on catalyst concentration, binder, size, etc., but is generally designed for 0.1–10 WHSV, based on total catalyst solids. In this description, metric units and parts by weight are employed unless otherwise stated.

The process of this invention may be used in a continuous process for reacting lower alkanol and a mixture of $C_4$-$C_7$ tertiary-alkenes in a multizone catalytic reactor to produce corresponding ethers. It has been found that reaction equilibrium is significantly different for $C_5$- and $C_6+$ tertiary alkenes. Catalytic activity at reaction temperature below 80+ C. decreases substantially from isopentene to isohexene and isoheptane. Conventional polysulfonic acid resin catalyst cannot provide the amount of activity realized by metallosilicates such as Zeolite Beta at the lower reaction temperatures which favor ether production from $C_6+$ isoalkenes. Accordingly, a multizone reactor system is advantageous for converting $C_4$-$C_7$ isoalkene mixtures. This is achieved by (a) maintaining a first bed of solid acid catalyst particles in a first reaction zone and a second bed of solid acid porous metallosilicate catalyst particles in a second reaction zone, said metallosilicate having a pore size of 5-8 Å and having active Bronsted acid sites; (b) contacting the alkanol and tertiary-alkene mixture with the first bed of solid acid catalyst particles under etherification conditions, typically above 80° C., to form a first ether product; (c) transporting unreacted alkanol and tertiaryalkene into contact with the second bed of catalyst particles maintained at lower temperature; and (d) further reacting the alkanol and tertiary-alkene in the second bed of catalyst particles at lower reaction temperature (i.e. below 80° C.) to produce additional ether product.

While the invention has been described by particular example, there is no intention to limit the inventive concept except as set forth in the following claims.

We claim:

1. In a continuous process for reacting volatile lower alkanol and tertiary-alkene in a catalytic distillation reactor vessel to produce a corresponding ether, the improvement which comprises:

maintaining a first bed of solid acid resin catalyst particles in a lower portion of the catalytic distillation reactor vessel and a second bed of solid acid porous metallosilicate catalyst particles in an upper portion of the reactor vessel, said metallosilicate having a pore size of 5-8 Å and having active Bronsted acid sites;

introducing at least one volatile reactant stream and contacting the alkanol and tertiary-alkene with the first bed of solid acid catalyst particles at a temperature between 65° and 90° C. at the bottom of the first bed to form ether product under etherification conditions;

maintaining catalytic distillation conditions in the first bed of solid acid catalyst particles to condense ether product for recovery as a liquid product stream while vaporizing and transporting unreacted volatile alkanol and tertiaryalkene into contact with the second bed of catalyst particles in an upper portion of the reactor vessel; and further reacting the volatile alkanol and tertiary-alkene in the second bed of catalyst particles at a reaction temperature between 40° and 60° C. at the top of the second bed to produce additional ether product.

2. The process of claim 1 wherein said metallosilicate catalyst comprises Zeolite Beta, said alkanol consists essentially of methanol, and said tertiary- alkene comprises isobutene, isopentene, isohexene, isoheptane or mixtures of said tertiary-alkenes.

3. The process of claim 2 wherein said tertiary-alkene consists essentially of isohexene.

4. A process for reacting methanol and tertiary-hexene in a catalytic distillation reactor vessel to produce methyl t-hexyl ether comprising the steps of contacting the methanol and tertiary-hexene under etherification conditions with a first bed of solid acid resin catalyst particles in the catalytic distillation reactor vessel at a temperature between 65° and 90° C. at the bottom of the first bed while maintaining a second bed of solid acid porous catalyst particles comprising metallosilicate having the structure of Zeolite Beta in an upper portion of the reactor vessel; and maintaining catalytic distillation conditions in the first bed of solid acid catalyst particles to condense ether product for recovery as a liquid product stream while vaporizing and transporting unreacted methanol and tertiary-hexene into contact with the second bed of catalyst particles in an upper portion of the reactor vessel at reaction temperature between 40° and 60° C. at the top of the second bed to produce additional ether product.

5. In a process for reacting volatile lower alkanol and tertiary-alkene in a catalytic distillation reactor vessel containing a first bed of solid acid resin catalyst particles at a temperature between 65° and 90° C. at the bottom of the first bed to produce a corresponding ether, the improvement which comprises:

maintaining an upper rectification distillation section in the catalytic distillation reactor vessel containing a second bed comprising solid acid porous metallosilicate catalyst particles having a pore size of 5-8 Å; and reacting the volatile alkanol and tertiary-alkene in the rectification section at a reaction temperature between 40° and 60° C. at the top of the second bed to produce ether product.

6. A continuous process for reacting lower alkanol and a mixture of $C_4$-$C_7$ tertiary-alkenes in a multizone catalytic distillation reactor to produce corresponding ethers, comprising the steps of:

maintaining a first bed of solid acid resin catalyst particles in a first reaction zone and a second bed of solid acid porous metallosilicate catalyst particles in an second reaction zone of said reactor, said metallosilicate having a pore size of 5-8 Å and having active Bronsted acid sites;

contacting the alkanol and tertiary-alkene mixture with the first bed of solid acid catalyst particles under etherification conditions at a temperature between 65° and 90° C. to form a first ether product;

transporting unreacted alkanol and tertiary-alkene into contact with the second bed of catalyst particles maintained at lower temperature between 40° and 60° C.; and further reacting the alkanol and tertiary-alkene in the second bed of catalyst particles at lower reaction temperature to produce additional ether product.

7. The process of claim 6 wherein said metallosilicate catalyst comprises Zeolite Beta, said alkanol consists essentially of methanol, and said tertiary-alkene mixture comprises isohexene.

* * * * *